United States Patent [19]

Buysch et al.

[11] Patent Number: 5,440,066
[45] Date of Patent: * Aug. 8, 1995

[54] PROCESS FOR SPLITTING POLYCARBONATES

[75] Inventors: Hans-Josef Buysch; Norbert Schön, both of Krefeld; Steffen Kühling, Meerbusch; Heinrich Hähnsen, Duisburg, all of Germany

[73] Assignee: Bayer Aktiengesellschaft, Leverkusen, Germany

[ * ] Notice: The portion of the term of this patent subsequent to Nov. 30, 2010 has been disclaimed.

[21] Appl. No.: 222,777

[22] Filed: Apr. 4, 1994

[30] Foreign Application Priority Data

Apr. 13, 1993 [DE] Germany .................. 43 12 037.7

[51] Int. Cl.$^6$ ............................................. C07C 68/06
[52] U.S. Cl. .............................. 558/277; 203/DIG. 6
[58] Field of Search ............................................. 558/277

[56] References Cited

U.S. PATENT DOCUMENTS 5,210,268  5/1993  Fukuoka et al. .................. 558/270
5,266,716 11/1993  Buysch et al. .................. 558/277 X

FOREIGN PATENT DOCUMENTS 1155452 10/1963 Germany .
  45600  5/1966 Germany .

Primary Examiner—Robert W. Ramsuer
Assistant Examiner—Michael G. Ambrose
Attorney, Agent, or Firm—Joseph C. Gil; Aron Preis

[57] ABSTRACT

A continuous process for splitting an aromatic polycarbonate resin is disclosed. Accordingly there are reacted in a distillation column and in the presence of a catalyst (i) a polycarbonate resin in solution with (ii) methanol to produce a dihydroxy compound and dimethyl carbonate. The solution which contains polycarbonate and monohydroxy compound solvent exclusive of methanol is fed into the upper section of said column and the methanol is fed into the lower section of the column. The methanol is fed in the form of a mixture containing methanol and about 1–50 weight percent of dimethyl carbonate. The dimethyl carbonate thus produced is removed from an upper section of the column and the dihydroxy compound is removed from a lower section of the column.

5 Claims, No Drawings

PROCESS FOR SPLITTING POLYCARBONATES

This invention relates a process for the continuous splitting of aromatic polycarbonates into dihydroxy compounds and dimethyl carbonate by catalytic transesterification of aromatic polycarbonates—dissolved in other monohydroxy compounds than methanol—with methanol in a distillation column, the polycarbonate solution being fed into the upper section of the column and the methanol into the lower section of the column and a dimethyl carbonate stream being removed from the upper section of the column and a stream of dihydroxy compounds from the lower section of the column, characterized in that the methanol to be used contains 1 to 50% by weight, preferably 2 to 40% by weight and, more preferably, 5 to 35% by weight, based on the total weight of methanol and dimethyl carbonate, of dimethyl carbonate.

It is known that polycarbonates can be split with hydroxy compounds into dialkyl carbonates and dihydroxy compounds. This process requires long reaction and residence times, so that product damage cannot be ruled out, and is only carried out in batches (DAS 11 55 452).

By contrast, the process according to the invention can be continuously carried out easily and with high yields. One particular advantage is that the transesterification can be carried out in one step to high conversion levels or may even be carried out quantitatively, depending on the mode of operation of the transesterification column, with simultaneous separation of the reaction products.

The polycarbonates to be split may be dissolved in the other monohydroxy compounds in the melt phase in an extruder and also in known mixing units, reaction vessels, etc.

The other monohydroxy compounds suitable for dissolving the polycarbonates in accordance with the invention are $C_{2-30}$ aliphatic monoalcohols, $C_{3-10}$ cycloaliphatic monoalcohols, $C_{7-30}$ araliphatic monoalcohols, $C_{6-10}$ hydroxyaryls, $C_{1-4}$ alkylphenols, $C_{1-4}$ alkoxyphenols and halophenols. Suitable aliphatic monoalcohols are primary and secondary aliphatic monoalcohols; suitable cycloaliphatic monoalcohols are secondary cycloaliphatic monoalcohols while suitable araliphatic monoalcohols are also primary and secondary araliphatic monoalcohols.

Examples of suitable other monohydroxy compounds are ethanol, propanol, isopropanol, butanol, secondary butanol, isobutanol, pentanols, hexanols, octanols, decanols, undecanols, dodecanols, stearyl alcohol, cyclopentanol, cyclohexanol, cyclooctanol, cyclododecanol, benzyl alcohol, phenyl ethanol, phenol, o-cresol, m-cresol, p-cresol, methoxyphenol, chlorophenol and isopropylphenol. Ethanol, propanol, butanol, cyclohexanol, benzyl alcohol, phenol and p-cresol are preferred, phenol and ethanol or mixtures thereof being particularly preferred.

The quantities of other monohydroxy compounds which are used to dissolve the aromatic polycarbonate are not critical and are generally in the range from 1 to 30 mol per mol aromatic carbonate structural unit corresponding to general formula (I):

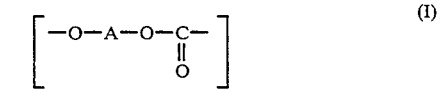

of the polycarbonate to be dissolved.

Particularly suitable other monohydroxy compounds are those which not only effectively dissolve the aromatic polycarbonates, but also initiate degradation of the polycarbonates by transesterification.

Primary alcohols, such as ethanol, propanol and n-butanol, and phenolic compounds, such as phenol itself, $C_{1-4}$ alkylphenols and halophenols, are preferably used for this purpose.

The quantity of methanol which is subsequently introduced from the lower section of the distillation column should be between 1.0 and 9.0 mol and preferably between 2.0 and 6.0 mol per mol aromatic carbonate structural unit (I) of the polycarbonate to be split.

It has now surprisingly been found that the use of dimethyl carbonate in accordance with the invention does not adversely affect transesterification of the polycarbonate with methanol, which does of course lead to the formation of dimethyl carbonate, but instead has a beneficial effect on the process according to the invention from the technical point of view.

Under the effect of the transesterification reaction according to the invention and the formation of dimethyl carbonate, the mixing ratio of methanol to dimethyl carbonate is displaced to high contents ($>40\%$ by weight and preferably $>50\%$ by weight) of dimethyl carbonate.

This mixture is removed at the head of the transesterification column and distilled into the azeotrope of 70% methanol and 30% dimethyl carbonate and pure dimethyl carbonate either in a separate continuously operating column or directly in a separation column surmounting the transesterification column, the pure dimethyl carbonate also be removable at a sidestream from the lower part of the separation column.

Accordingly, pure dimethyl carbonate can ultimately be obtained without difficulty and the azeotropic mixture of methanol and dimethyl carbonate removed may be reused for the transesterification, optionally fresh methanol and also dimethyl carbonate being added.

However, unseparated mixture of methanol and dimethyl carbonate containing more than 30% dimethyl carbonate may also be reused for the transesterification. Accordingly, the transesterification process according to the invention not only was not obvious, it also has the advantage of producing pure dimethyl carbonate.

This is of particular value because transesterifications with methanol are generally accompanied by the formation of mixtures of methanol and dimethyl carbonate with relatively low contents of dimethyl carbonate because methanol and dimethyl carbonate form an azeotrope containing 70% by weight methanol. The production of dimethyl carbonate by various methods also gives mixtures with low dimethyl carbonate contents which are difficult and expensive to separate (cf. DAS 26 15 665, DE 2 706 684, U.S. Pat. No. 4,218,391, Industr. Eng. Chem. Prod. Res. Dev. 19, 396–403 (1980), EP 894, EP 225 252, EP 298 167). Accordingly, the effect of the process according to the invention is that:

1. methanol/dimethyl carbonate azeotrope is removed at the head of the separation column and returned to the process according to the invention, 2. pure dimethyl carbonate is removed as a sidestream in the lower part or at the bottom of the separation column and may be used for organic syntheses, etc., for example for the production of diphenyl carbonate in accordance with EP 461 274;
3. the diphenols obtained and any quantities of the other monohydroxy compounds still present are removed at the bottom of the transesterification column and may be separated in known manner, the other monohydroxy compounds again being used to dissolve other aromatic polycarbonates for use in the process according to the invention and the diphenols being used for organic syntheses, etc.

The use of phenolic compounds, particularly phenol, as other monohydroxy compounds has the following advantage that, for example in the splitting of bisphenol A polycarbonate in accordance with the invention, the bisphenol A formed may be obtained in crystalline form as the known 1:1 adduct with phenol.

Accordingly, the present invention also relates preferably to the process according to the invention in which phenolic compounds are used as other monohydroxy compounds.

In a variant of the process according to the invention, methanol is added in quantities of 0 to 1 mol per mol polycarbonate unit (I) to the polycarbonate solution in the upper part of the distillation column. The quantity by weight of other monohydroxy compounds can thus be reduced accordingly. The quantity of methanol/dimethyl carbonate mixture to be introduced into the lower section of the distillation column may be reduced accordingly.

This variant of the process has the advantage that, even before it is introduced into the column, the methanol may be partly converted into dimethyl carbonate, thus relieving the column of load.

Accordingly, the present invention also relates to the process according to the invention in which the other monohydroxy compound is partly replaced by methanol.

In another variant of the process according to the invention, polycarbonate solvents free from OH groups are additionally used in quantities by weight of 0.1 to 10 times and preferably in quantities by weight of 0.1 to 5 times the weight of the polycarbonate to be split. However, it is preferred not to use any solvent. Suitable polycarbonate solvents free from OH groups are, for example, hydrocarbons such as toluene, xylenes, cumene, cymol, trimethyl benzene, tetramethyl benzenes, diisopropyl benzenes, tetralin, naphthalene, biphenyl; ethers such as dibutyl ether, dioxane, dimethyl diglycol, diethyl triglycol, dimethyl tetraglycol, anisole, phenylbutyl ether, methoxytoluenes, dimethoxybenzenes, diphenyl ethers; halogenated hydrocarbons, such as chlorobenzene, dichlorobenzene, bromobenzene, dibromobenzenes, chloronaphthalenes, chlorotoluenes, chloroxylenes, chlorocumenes; and amides, such as dimethyl acetamide, N-acetyl morpholine, N,N-dimethyl benzamide.

This variant of the process has the advantage that any solid impurities present in the polycarbonate can be filtered off more easily by reducing the viscosity.

Accordingly, the present invention also relates to the process according to the invention, in which 0.1 to 10 times the quantity by weight of the polycarbonate of polycarbonate solvents free from OH groups is used in addition to the other monohydroxy compounds.

Accordingly, a suitable combination is, for example, phenol or ethanol as other monohydroxy compounds to which approx. 5% by weight methanol and/or also 10% by weight $CH_2Cl_2$, based on the weight of phenol or ethanol, has been added.

Suitable other combinations may readily be calculated and formulated in accordance with the above figures.

In the most simple case, the distillation column used for the process according to the invention is an isothermally heated tube filled with packings typically used for distillation processes. The transesterification steps are completed surprisingly quickly in the tube so that, even with a relatively short column of this simple construction, considerable quantities of carbonic acid esters distill over at the head of the column.

However, the column may also comprise a stripping section operating at higher temperatures at its lower end. In this stripping section, the monohydroxy compound is largely or completely separated from the dihydroxy compound flowing down and returned to the transesterification section of the column.

In addition, the column may have a concentrating section operating at low temperature at its upper end in order to complete the separation of gaseous methanol and dimethyl carbonate from relatively high boilers, for example phenol, so that a pure or substantially pure mixture of monohydroxy compound and carbonic acid, may be removed at the head of the column.

Energy may be supplied through the methanol/dimethyl carbonate mixture introduced into the column in the gas phase and/or through the bottom evaporator. The mixture may even be introduced in liquid form, in which case energy has to be supplied through the bottom evaporator. In the first case, the middle section of the column, in which most of the transesterification process takes place, may be widened in diameter by up to four times the diameters of the other sections. In the second case, the enthalpy of evaporation for the methanol/dimethyl carbonate mixture must be transported through the stripping section where it leads to a high gas and liquid load. This results in widening of the column in the stripping section to guarantee the separations to be effected therein. The widening and length of the stripping section depend upon the fittings selected for the column in the stripping section which may be laid out by the expert.

Since two molecules of methanol can be replaced by one molecule of dimethyl carbonate during transesterification in the gas phase, a reduction in cross-sectional area by a factor of up to 2 can be of advantage to keep the gas flow rate in the middle section of the column at a constant level.

Accordingly, the column can be isothermally heated and, preferably, equipped with one or more temperature zones different from the main section, resulting in a temperature gradient with downwardly increasing values.

The packing elements or tower packs to be used are known per se for distillation and are described, for example, in Ullmann's Encyclopädie der Technischen Chemie, 4th Edition, Vol. 2, pages 528 et seq. or in company brochures published by the relevant manufacturers. Suitable packing elements are, for example, Raschig or Pall rings, Berl-Intalex saddles or Torus saddles, Interpack elements of various materials, such as glass, stoneware, porcelain, carbon, stainless steel, plastics, which may be made up into woven or mesh-like cloth, particularly where metal is used. It is preferred to use packing elements and tower packings characterized by a large surface, thorough wetting and an adequate residence time of the liquid. Examples of such packs and packing elements are Pall and Novolax rings, Berl saddles, BX packs, Montz-Pak, Mellapak, Kerapak and CY packs.

However, not only packed columns, but also columns with permanent fittings may also be used for the process according to the invention. Among columns such as these, those fitted with bubble cap or valve plates with long residence times and good mass transfer are preferred.

Other plate columns are also generally suitable, for example plate columns with sieve, bubble cap, valve, tunnel and centrifugal plates, which may be present in various designs.

Catalysts suitable for the splitting of polycarbonates in accordance with the invention are known from the literature (see, for example, DDR patents 45 600 and 46 363, DE-AS 1 155 452 and JA 61/27 203A). Suitable catalysts are, for example, hydrides, oxides, hydroxides, alcohols, amides or salts of alkali metals, such as lithium, sodium, potassium, rubidium and caesium, preferably lithium, sodium and potassium and, more preferably, sodium and potassium. Salts of alkali metals are those of organic and inorganic acids, for example acetic acid, propionic acid, butyric acid, benzoic acid, stearic acid, carbonic acid, hydrochloric acid, HBr, HI, nitric acid, $H_2SO_4$, HF, phosphoric acid, boric acid, acids of tin and acids of antimony.

Preferred alkali metal catalysts are alkali metal oxides, hydroxides, alcoholates, acetates, propionates, benzoates, carbonates and hydrogen carbonates; particularly preferred alkali metal catalysts are the alkali metal hydroxides, alcoholates, acetates, benzoates and carbonates.

The alkali metal catalysts are used in quantities of 0.0001 to 20 mol-%, preferably in quantities of 0.001 to 10 mol-% and, more preferably, in quantities of 0,005 to 5 mol-% per mol carbonate unit in the polycarbonate to be split.

The alkali metal catalysts may optionally be used in combination with complexing agents, such as for example crown ethers, polyethylene glycols or bicyclic nitrogen-containing cryptands.

One example of a suitable crown ether is dibenzo-18-crown-6; one example of a suitable nitrogen-containing cryptand is 1,9-dimethyl-1,6-diazadibenzo-18-crown-6.

The complexing agents are used in quantities of 0.1 to 200 mol-% and preferably in quantities of 1 to 100 mol-%, based on 1 mol alkali metal compound.

Other suitable catalysts for the splitting of polycarbonates in accordance with the invention are nitrogen-containing bases, such as for example secondary and tertiary amines, such as triethylamine, tributylamine, methyl dibenzylamine and dimethyl cyclohexylamine, diazabicycloundecane or diazabicyclononane.

The nitrogen-containing bases are used in quantities of 0.001 to 20 mol-%, preferably in quantities of 0.005 to 10 mol-% and, more preferably, in quantities of 0.01 to 3 mol-%, based on 1 mol carbonate unit in the polycarbonate to be split.

Other suitable catalysts for the splitting of polycarbonates in accordance with the invention are complexes or salts or compounds of magnesium, calcium, barium, zinc, tin, titanium or zirconium. Examples of such systems are tin methoxide, dimethyl tin, dibutyl tin oxide, dibutyl tin dilaurate, tributyl tin hydride, tributyl tin chloride, tin(II) ethyl hexanoates, zirconium alkoxides (methyl, ethyl, butyl), zironium(IV) halides (F, Cl, Br, I), zirconium nitrate, zirconium acetyl acetonate, titanium alkoxides (methyl, ethyl, isopropyl), titanium acetate and titanium acetyl acetonate.

The catalysts are used in quantities of 0.0001 to 20 mol-%, preferably in quantities of 0.001 to 10 mol-% and more preferably in quantities of 0.005 to 5 mol-%, based on 1 mol carbonate unit in the polycarbonate to be split.

The catalysts to be used are introduced either as such or in polycarbonate solution. The catalysts to be used for the splitting of polycarbonates may also be dissolved in the monohydroxy compound to be used for the transesterification reaction and separately added to the polycarbonate solution via the head of the distillation column to be used. Where alkali metal catalysts are used, alkali metal alcoholates may be produced in situ.

In cases where a heterogeneous catalyst completely or substantially insoluble in the reactants is used, it may even be introduced beforehand in admixture with the packing elements of the distillation column or as a packing on incorporated column plates or may be incorporated in the column in the form of a pack.

The distillation column to be used in accordance with the invention is preferably operated by introducing the polycarbonate solution and optionally the catalyst, whether as such or in solution, into the upper half and preferably into the upper third of the column.

The polycarbonate preferably has the same temperature which prevails in the column at the point of introduction.

The methanol/dimethyl carbonate mixture used to split the polycarbonate is introduced into the lower half of the column, preferably above any stripping zone present.

The methanol/dimethyl carbonate mixture used for the polycarbonate splitting process is preferably introduced in vapor form. If it is introduced in liquid form, it must be evaporated via the bottom evaporator, as already mentioned.

At the head of the column, the methanol/dimethyl carbonate mixture is removed and condensed, preferably after passing through a concentrating zone. It may optionally contain small amounts of other monohydroxy compound present in the system. A solution or melt of the dihydroxy compound(s) on which the polycarbonate is based is removed from the bottom of the column under carefully established conditions and may be worked and and purified by known methods, for example by distilltion and/or crystallization, or otherwise.

The temperature in the column is in the range from 50° to 200° C., preferably in the range from 60° to 190° C. and more preferably in the range from 70° to 180° C. Any temperature gradient to be applied is situated in the temperature range mentioned and increases from the head to the bottom of the column.

In general, the reaction on which the process according to the invention is based is carried out at normal pressure. However, it may also be carried out under a slightly elevated pressure of up to about 5 bar, preferably up to 4 bar and more preferably up to 3 bar, or under a reduced pressure of up to 50 mbar, preferably up to 100 mbar and, more preferably, up to 200 mbar. The distillate to be removed, for example, at the head of the column may be influenced in known manner by applying a pressure different from normal pressure.

The volume/time load of the column is in the range from 0.1 to 5.0 g total quantity of reactants per ml effective column volume per hour, preferably in the range from 0.2 to 4 g/ml/h and, more preferably, in the range from 0.3 to 3.0 g/ml/h; the effective column volume is the volume of the packing or the volume in which fixed elements are situated.

Polycarbonates in the context of the invention are generally those based on aromatic dihydroxy compounds of the type which are, and may be, used on an industrial scale.

Aromatic dihydroxy compounds are, for example, dihydroxybenzenes, dihydroxybiphenyl, dihydroxydiphenyl ether, dihydroxydiphenyl sulfide, dihydroxydiphenyl sulfone, dihydroxydiphenyl methane (bisphenol F), dihydroxydiphenyl ethane, dihydroxydiphenyl propane (bisphenol A), dihydroxydiphenyl cyclohexane (bisphenol Z), 3,3,5-trimethyl-1,1-(dihydroxydiphenyl)-cyclohexane, $\alpha,\alpha'$-(dihydroxyphenyl)-diisopropyl benzenes, dihydroxybenzophenone or mixtures of these aromatic dihydroxy compounds, preferably bisphenol A, bisphenol Z, dihydroxydiphenyl methane and 3,3,5-trimethyl-1,1-(dihydroxydiphenyl)-cyclohexane. Bisphenol A is particularly preferred.

The polycarbonates to be split in accordance with the invention are known from the literature (see, for example, H. Schnell "Chemistry and Physics of Polycarbonates", Interscience Publishers, New York, 1964).

The polycarbonates to be split may have molecular weights Mw (weight average as determined, for example, by gel permeation chromatography) in the range from 5,000 to 200,000 and preferably in the range from 10,000 to 80,000. The molecular weights may also be determined in known manner by measurement of the relative viscosity in $CH_2Cl_2$ at 25° C. and at a concentration of 0.5% by weight. Preferred polycarbonates to be split in accordance with the invention are the aromatic thermoplastic polycarbonates which are preferably produced from at least one of the diphenols mentioned below:

4,4'-dihydroxydiphenyl, 2,2-bis-(4-hydroxyphenyl)-propane (bisphenol A), 2,4-bis-(4-hydroxyphenyl)-2-methylbutane, 1,1-bis-(4-hydroxyphenyl)-cyclohexane, $\alpha,\alpha'$-bis-(4-hydroxyphenyl)-p-diisopropyl benzene, 2,2-bis-(3-chloro-4-hydroxyphenyl)-propane, 2,2-bis-(3,5-dichloro-4-hydroxyphenyl)-propane, 2,2-bis-(3,5-dibromo-4-hydroxyphenyl)-propane and 1,1-bis-(4-hydroxyphenyl)-3,3,5-trimethyl cyclohexane.

The polycarbonates to be split in accordance with the invention may also be branched in known manner by the incorporation of trifunctional or more than trifunctional compounds.

They are collected together with the dihydroxy compounds at the bottom of the distillation column as a result of splitting in accordance with the invention and may optionally be isolated by crystallization.

Where they are monophenols, the chain terminators released from the polycarbonates to be split in accordance with the invention are also collected at the bottom of the distillation column and optionally isolated in known manner. Where aliphatic or cycloaliphatic monoalcohols are incorporated as chain terminators in the polycarbonates to be split, they may be removed for example as dialkyl carbonates at the head of the distillation column.

The process according to the invention for the splitting of polycarbonates may be generally used for various polycarbonate molding compounds. However, it is not just used to synthesize dihydroxy compounds and dimethyl carbonate in this way, but above all chemically to split polycarbonate molding compounds which cannot otherwise be utilized, i.e. waste accumulating for example in the production of moldings, cuttings or reject moldings, polycarbonate waste etc., into monomeric components which may readily be purified and hence reused for the production of polycarbonates or for other purposes; the dihydroxy compounds, for example, for the production of epoxy resins or polyurethanes and the carbonic acid esters as solvents or for syntheses in organic chemistry.

Accordingly, the polycarbonates to be split in accordance with the invention may contain the usual additives, such as mineral fillers, for example silica flour, glass powder, glass fibers, stabilizers, UV stabilizers, lubricants, pigments, dyes, also polymeric blend components, such as for example vinyl polymers of styrene, acrylonitrile and butadiene.

Those additives which are insoluble in the polycarbonate solution are removed by filtration, centrifugation or sedimentation before the solution is introduced into the transesterification column. Those additives which are soluble in the polycarbonate solution may be separated from the dihydroxy compounds obtained by distillation or crystallization.

Coloring impurities introduced by the polycarbonate used can be removed not only by distillation or crystallization, but also by adsorptive purification techniques, for example on active carbon, kieselguhr, cellulose or zeolites. The adsorptive purification processes may be carried out both with the polycarbonate solution before the splitting process according to the invention and with the solutions of the dihydroxy compounds accumulating at the bottom of the distillation column.

The polycarbonate splitting process according to the invention is therefore eminently suitable for the recycling of polycarbonate waste.

Comparison Example 1 (corr. to DAS 11 55 452)

254 g granulated bisphenol A polycarbonate, molecular weight approx. 28,000, 0.5 g NaOH and 160 g methanol were boiled under reflux. After 10 h, the reaction was terminated and the mixture was worked up by distillation, too little dimethyl carbonate distilling over. Accordingly, more methanol was added until no more dimethyl carbonate distilled over. The total reaction time was 19 h. 82 g dimethyl carbonate distilled over. 179 g brownish crystals were obtained from the brown bottom product by recrystallization from toluene.

Comparison Example 2

In an 80 cm long tube approx. 5 cm in diameter, 1 g dibutyl tin dioxide and 50 g methanol were added to 1,000 g of a 10% solution of bisphenol A polycarbonate, molecular weight approx. 28,000, in o-dichlorobenzene and, after heating to 90° to 100° C., 10 to 15 g methanol vapor per hour were introduced through a base frit. The distillate distilling over was collected. The reaction was terminated after 21 h. Approx. 34 g dimethyl carbonate were obtained in the distillate. The sump was a brown solution containing approx. 85 g bisphenol A. After working up, bisphenol A was obtained in the form of brown crystals.

Example 1

500 g/h of a 40% bisphenol A polycarbonate solution in phenol (molecular weight approx. 28,000) containing 1% by weight octyl stannonic acid, based on polycarbonate, are introduced at the fourth plate of a 20-plate bubble plate column 5 cm in diameter of which the heating jacket and circulation evaporator are respectively thermostated to 150° C. and 170° C. 150 g/h of a vapor consisting of 80% by weight methanol and 20% by weight dimethyl carbonate are introduced in countercurrent to the polycarbonate solution from below through an evaporator adjusted to 150° C. A quantity of 500 to 510 g of a bottom product containing 176 to 180 g bisphenol A and 170 to 173 g of a head product containing 60 to 61% dimethyl carbonate are obtained per hour. The conversion and selectivity are substantially quantitative.

Example 2

500 g/h of a 40% bisphenol A polycarbonate solution in phenol (molecular weight approx. 28,000) containing 0.3% by weight KOH, based on polycarbonate, are introduced at the fourth plate of a 20-plate bubble plate column 5 cm in diameter of which the heating jacket and circulation evaporator are respectively thermostated to 150° C. and 170° C. 160 g/h of a vapor consisting of 50% by weight methanol and 50% by weight dimethyl carbonate are introduced in countercurrent to the polycarbonate solution from below through an evaporator adjusted to 150° C. A product containing 83% dimethyl carbonate is obtained at the head of the column (approx. 180 kg/h) and a solution of bisphenol A in phenol at the bottom of the column. The conversion and selectivity are substantially complete.

Example 3

The repetition of Example 2 with 100 g/h of a mixture of 70% by weight methanol and 30% by weight dimethyl carbonate gives 119-122 g/h of a head product containing 83-85% by weight dimethyl carbonate. The conversion and yield are substantially quantitative.

What is claimed is:

1. A continuous process for splitting an aromatic polycarbonate resin comprising reacting in a distillation column and in the presence of a catalyst
    (i) a polycarbonate resin in solution with
    (ii) methanol
to produce a dihydroxy compound and dimethyl carbonate, wherein said solution contains polycarbonate and monohydroxy compound solvent exclusive of methanol, and wherein said solution is fed into the upper section of said column and wherein said methanol is fed into the lower section of said column in the form of a mixture containing methanol and dimethyl carbonate, and wherein dimethyl carbonate thus produced is removed from an upper section of said column and wherein said dihydroxy compound thus produced is removed from a lower section of said column and wherein said mixture contains about 1 to 50% of dimethyl carbonate, said percent being relative to the weight of said mixture.

2. The process of claim 1 wherein said mixture contains about 2 to 40% by weight of dimethyl carbonate.

3. The process of claim 1 wherein said monohydroxy compound is a phenolic compound.

4. The process of claim 1 wherein said solution contains a minor amount of methanol.

5. The process of claim 1 wherein said solution further contains solvents which are free of OH groups.

* * * * *